United States Patent
Pedicini (10) Patent No.: US 8,393,409 B2
(45) Date of Patent: Mar. 12, 2013

(54) ELECTRIC MOTOR DRIVEN TOOL FOR ORTHOPEDIC IMPACTING

(75) Inventor: Christopher Pedicini, Nashville, TN (US)

(73) Assignee: Ortho Technologies, LLC, Flagstaff, AZ (US)

( * ) Notice: Subject to any disclaimer, the term of this patent is extended or adjusted under 35 U.S.C. 154(b) by 0 days.

(21) Appl. No.: 13/466,870

(22) Filed: May 8, 2012

(65) Prior Publication Data

US 2012/0215267 A1 Aug. 23, 2012

Related U.S. Application Data

(63) Continuation of application No. 13/337,075, filed on Dec. 24, 2011, now abandoned, and a continuation-in-part of application No. 12/980,329, filed on Dec. 29, 2010.

(51) Int. Cl.
*B25D 17/00* (2006.01)

(52) U.S. Cl. ............ 173/201; 173/2; 173/109; 173/132; 173/168

(58) Field of Classification Search .................. 173/201, 173/176, 2, 132, 114, 48, 217, 104, 109
See application file for complete search history.

(56) References Cited

U.S. PATENT DOCUMENTS

| | | | |
|---|---|---|---|
| 974,267 A * | 11/1910 | Hennessey et al. ........... | 173/201 |
| 3,712,390 A * | 1/1973 | Berg .............................. | 173/132 |
| 4,143,585 A | 3/1979 | Selsam | |
| 4,442,906 A * | 4/1984 | Simpson .......................... | 173/48 |
| 5,057,112 A | 10/1991 | Sherman et al. | |
| 5,108,400 A | 4/1992 | Appel et al. | |
| 5,167,043 A * | 12/1992 | Lopez et al. ....................... | 7/144 |
| 5,980,528 A | 11/1999 | Salys | |
| 6,112,830 A * | 9/2000 | Ziegler et al. .................. | 173/109 |
| 6,520,266 B2 * | 2/2003 | Bongers-Ambrosius et al. ................. | 173/2 |
| 6,644,418 B2 * | 11/2003 | Haga ............................... | 173/48 |
| 6,938,705 B2 * | 9/2005 | Kikuchi .......................... | 173/201 |
| 7,001,393 B2 | 2/2006 | Schwenke et al. | |
| 7,318,485 B2 * | 1/2008 | Greese et al. ....................... | 173/1 |
| 7,383,895 B2 * | 6/2008 | Aoki .............................. | 173/201 |
| 7,708,083 B2 | 5/2010 | Dreisig et al. | |
| 7,708,739 B2 | 5/2010 | Kilburn et al. | |
| 7,784,562 B2 * | 8/2010 | Ikuta .............................. | 173/201 |
| 7,861,799 B2 * | 1/2011 | Iwakami et al. ............... | 173/201 |
| 7,926,584 B2 | 4/2011 | John et al. | |
| 8,069,929 B2 * | 12/2011 | Sugimoto et al. ............. | 173/128 |

* cited by examiner

*Primary Examiner* — Scott A. Smith
(74) *Attorney, Agent, or Firm* — Aidenbaum Schloff and Bloom PLLC; Jay Schloff (57) ABSTRACT

An orthopedic impacting tool comprises a motor, a linear motion converter, an air chamber, a compression piston, a striker, a detent and a broach adapter. The compression piston may cause the striker to apply controlled force on a adapter to create a precise opening for subsequently disposing a prosthesis in a patient. The detent may hold the striker in a position until a sufficient pressure is applied to release the striker. The tool allows forward or backward impacting for expanding the size or volume of the opening or for facilitating removal of the broach and tool from the opening. A force adjustment control of the tool allows a user to increase or decrease the impact force. A light source and hand grips improve ease of operation of the tool.

19 Claims, 6 Drawing Sheets

ELECTRIC MOTOR DRIVEN TOOL FOR ORTHOPEDIC IMPACTING

CROSS REFERENCE TO RELATED APPLICATIONS

The present application is a a continuation of and claims priority under 35 U.S.C. §120 on the U.S. patent application Ser. No. 13/337,075 filed Dec. 24, 2011, now abandoned, and is a continuation-in-part of and claims priority under 35 U.S.C. §120 on the pending U.S. patent application Ser. No. 12/980,329, filed Dec. 29, 2010, the disclosures of which are incorporated by reference.

FIELD

The present disclosure relates to electric tools for impacting in orthopedic applications, and, more particularly, to an electric motor driven tool for orthopedic impacting that is capable of providing controlled impacts to a broach, chisel, or other device for creating an opening in an area (in a bone structure, for example) to securely receive prosthesis within the area.

In the field of orthopedics, prosthetic devices such as artificial joints, are often implanted or seated in a patient's body by seating the prosthetic device in a cavity of a bone of the patient. The cavity must be created before the prosthesis is seated or implanted, and traditionally, a physician may remove worn, excess, or diseased bone structure from the area in which the cavity will be formed, and then drill and hollow out a cavity along the medullar canal of the bone. A prosthesis usually includes a stem or other protrusion that serves as the particular portion of the prosthesis that is inserted into the cavity.

To create such a cavity, a physician may use a broach, which broach conforms to the shape of the stem of the prosthesis. Solutions known in the art include providing a handle with the broach, which handle the physician may grasp while hammering the broach into the implant area. Unfortunately, this approach is clumsy and unpredictable as being subject to the skill of the particular physician. This approach almost will always inevitably result in inaccuracies in the location and configuration of the cavity. Further, this approach carries with it the risk that the physician will damage bone structure in unintended areas.

Another technique for creating the prosthetic cavity is to drive the broach pneumatically, that is, by compressed air. This approach is disadvantageous in that it prevents portability of an impacting tool, for instance, because of the presence of a tethering air line, air being exhausted from a tool into the sterile operating field and fatigue of the physician operating the tool. Further this approach, as exemplified in U.S. Pat. No. 5,057,112 does not allow for precise control of the impact force or frequency and instead functions very much like a jackhammer when actuated. Again, this lack of any measure of precise control makes accurate broaching of the cavity more difficult.

Another disadvantage of tools known in the art is the accumulation of fluids, such as body fluids or moisture, on handgrips of such tools during prolonged periods of use. For example, difficulty of operation of a broach impacting device known in the art may increase during a surgical procedure as handgrips may become saturated with bodily fluids and thus the physician's hold on such a prior art device may become impaired.

Consequently, there exists a need for an impacting tool that overcomes the various disadvantages in the prior art.

In view of the foregoing disadvantages of the prior art, an electric motor-driven orthopedic impacting tool configured to include all the advantages of the prior art, and to overcome the drawbacks inherent therein is provided. The tool may be used by orthopedic surgeons for orthopedic impacting in for example hips, knees, and shoulders. The tool is capable of holding a broach, chisel, or other device and gently tapping the broach, chisel or other device into the cavity with controlled percussive impacts, resulting in a better fit for the prosthesis or the implant. Further, the control afforded by such an electrically manipulated broach, chisel, or other device allows adjustment of the impact settings according to a particular bone type or other profile of a patient. The tool additionally enables proper seating or removal of the prosthesis or the implant into or out of an implant cavity.

In an embodiment, an electric motor-driven orthopedic impacting tool comprises a control means, a housing, a linear motion converter, at least one reducing gear, an impacting element (also referred to herein as a striker), an air chamber, a compression piston, and a force adjustment control. The tool may further include a motor, an LED, a handle portion with at least one handgrip for comfortable gripping of the tool, an adapter, a battery, a feedback system and a nose-piece for the adapter. At least some of the various components are preferably contained within the housing. The tool is capable of applying cyclic impact forces on a broach, chisel, or other device, or an implant and of finely tuning impact force to a plurality of levels of impact force.

In an embodiment, the tool further comprises a control means, which means includes a force adjustment control (alternatively referred to herein as "force adjuster"), and which force adjustment control may control the impact force and avoid damage caused by uncontrolled impacts. The force may be regulated electronically or through the use of mechanical detents. The mechanical detent allows for an increased impact force without sacrificing control or precision of the broach machining operation.

The tool further may comprise an anvil element (alternatively referred to herein as "anvil"), which anvil includes both a forward and rearward point of impact and a guide that constrains the striker to move in a substantially axial direction. In operation, the movement of the striker along the guide of the anvil continues in either a forward or rearward direction until the striker hits the point of impact. As used in this context, "forward direction" connotes movement of the striker toward a broach or patient, and "rearward direction" connotes movement of the striker away from the broach or chisel or patient. If the impact point is at the front of the tool, i.e., in a forward direction, the impact causes the percussive force to be transmitted to a broach or chisel, pushing it further into the cavity. If the impact point is at the rear of the tool, the percussive force tends to pull the broach or chisel out of the cavity. The selectivity of either bidirectional or unidirectional impacting provides flexibility to a surgeon in either cutting or compressing material within the implant cavity, in that the choice of material removal or material compaction is often a critical decision in a surgical procedure. The impact point may be in the form of an plate that is disposed at an end or each end of the anvil.

The tool is further capable of regulating the frequency of the striker. By regulating the frequency of the striker, the tool may impart a greater total time-weighted percussive impact, while maintaining the same impact magnitude. This allows for the surgeon to control the cutting speed of the broach or chisel. For example, the surgeon may choose cutting at a faster rate (higher frequency impacting) during the bulk of the broach or chisel movement and then slow the cutting rate as the broach or chisel approaches a desired depth.

A user may firmly hold the tool by the handle portion and utilize light emitted by the LED to light up a work area and accurately position the broach, chisel, or other device on a desired location on the prosthesis or the implant. The reciprocating movement imparted on broach, chisel, or other device causes tapping of the implant and/or broach, chisel, or other device and thereby enables proper seating or removal of a prosthesis or implant into or out of an implant cavity, or controlled impacting of a broach, chisel, or other device to create or shape an implant cavity. The tool may also include a feedback system that warns the surgeon, when a bending or off-line orientation beyond a certain magnitude is detected at a broach, chisel, or other device/implant interface.

These together with other aspects of the present disclosure, along with the various features of novelty that characterize the present disclosure, is pointed out with particularity in the claims annexed hereto and forms a part of this present disclosure. For a better understanding of the present disclosure, its operating advantages, and the specific objects attained by its uses, reference should be made to the accompanying drawing and descriptive matter in which there are illustrated exemplary embodiments of the present disclosure.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like references numerals refer to like parts throughout the description of several views of the drawings.

LIST OF ELEMENTS IN FIGURES

1 Adapter
2 Air Compression Chamber Inlet Holes
3 Broach
4 Striker
5 Air Compression Chamber
6 Compression Piston
7 Gear Reducer
8 Motor
9 Striker Nose
10 Detent
11 Striker guide
12 Linear Motion Converter
13 Stroke Limiter
14 Anvil
15 Rear of Striker guide
16 Anvil forward impact surface
17
18 Force Adjuster
19 Air Passageway
20 Striker guide vent holes
21 Control means
22 Sensor

DETAILED DESCRIPTION OF THE DISCLOSURE

The best mode for carrying out the present disclosure is presented in terms of its preferred embodiment, herein depicted in the accompanying figures. The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The terms "a" and "an" herein do not denote a limitation of quantity, but rather denote the presence of at least one of the referenced items.

The present disclosure provides an electric motor-driven orthopedic impacting tool with controlled percussive impacts. The tool includes the capability to perform single or multiple impacts as well as impacting of variable directions, forces and frequencies. The impact force is adjusted by controlling the amount of air volume in the air chamber when the striker is released. This can be done very simply by way of a needle valve, for example (not shown) as the force adjuster 18. The detent used in this device has been advantageously determined to be magnetically operated although it will be apparent that other detent mechanisms may be employed. The detent facilitates the generation of a sufficient strike force to make a meaningful impact in the broach, chisel, or other device, or surgical area.

The tool includes a housing. The housing securely covers and holds a plurality of components of the tool. In an embodiment, the housing contains a motor, at least one reducing gear, a linear motion converter, a compression chamber, a striker, a force adjuster, a control means, and an anvil with a forward impact surface and a surface for rearward impact (which impact surface may be part of the anvil, part of the striker guide, or part of a broach adapter, for example).

The tool further may include a handle portion with at least one hand grip for comfortable and secure holding of the tool while in use, an adapter, a battery, a positional sensor, a directional sensor, and a torsion sensor. The tool may further comprise a lighting element such as an LED to provide light in the work area in which a user employs the tool. The anvil may be coupled to the broach through the use of the adapter. Such adapter may have a quick connect mechanism to facilitate rapid change of different broaching sizes.

Figure 1:
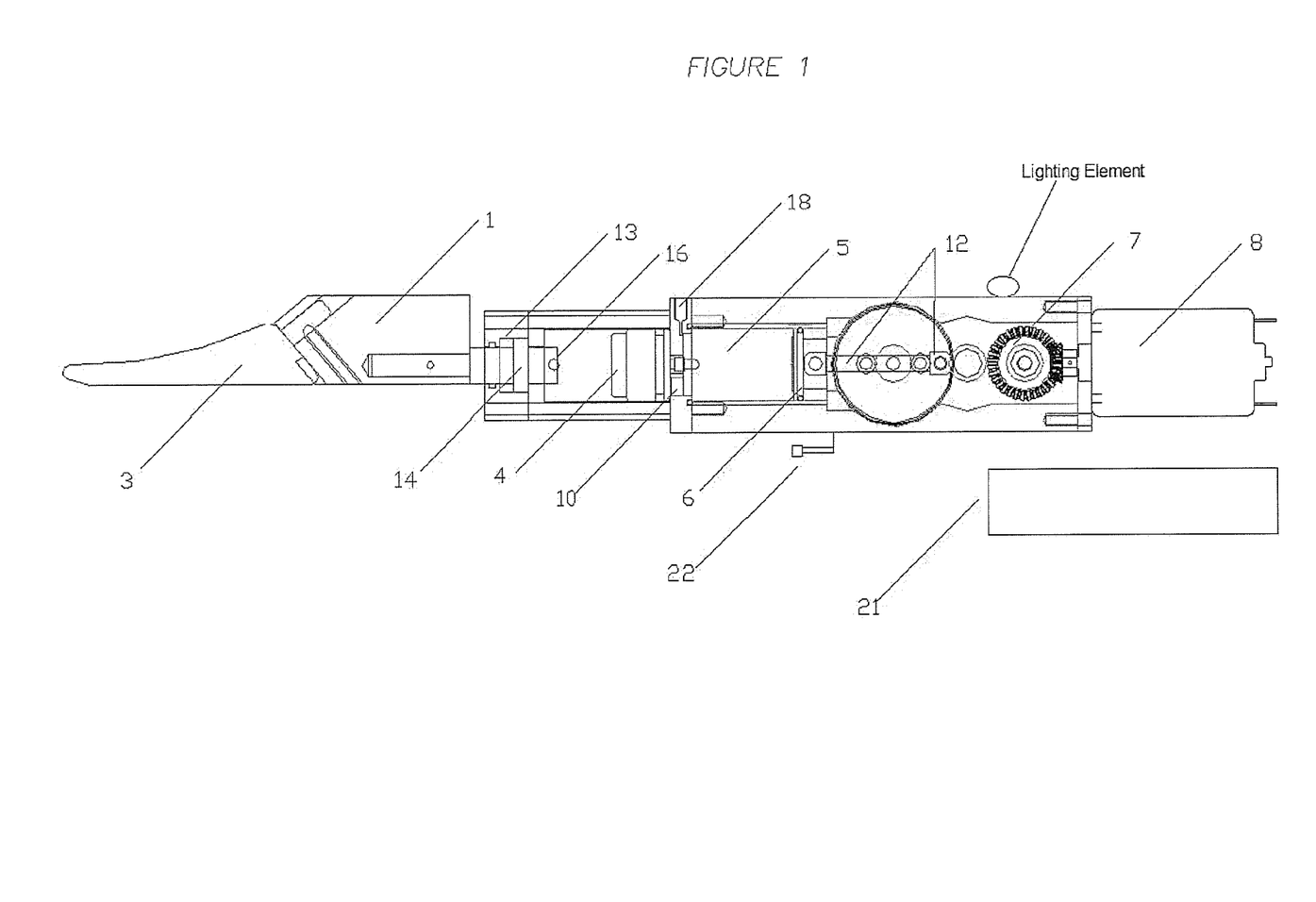
FIG. 1 shows a perspective view of an orthopedic impacting tool, in accordance with an exemplary embodiment of the present disclosure.
Figure 2:
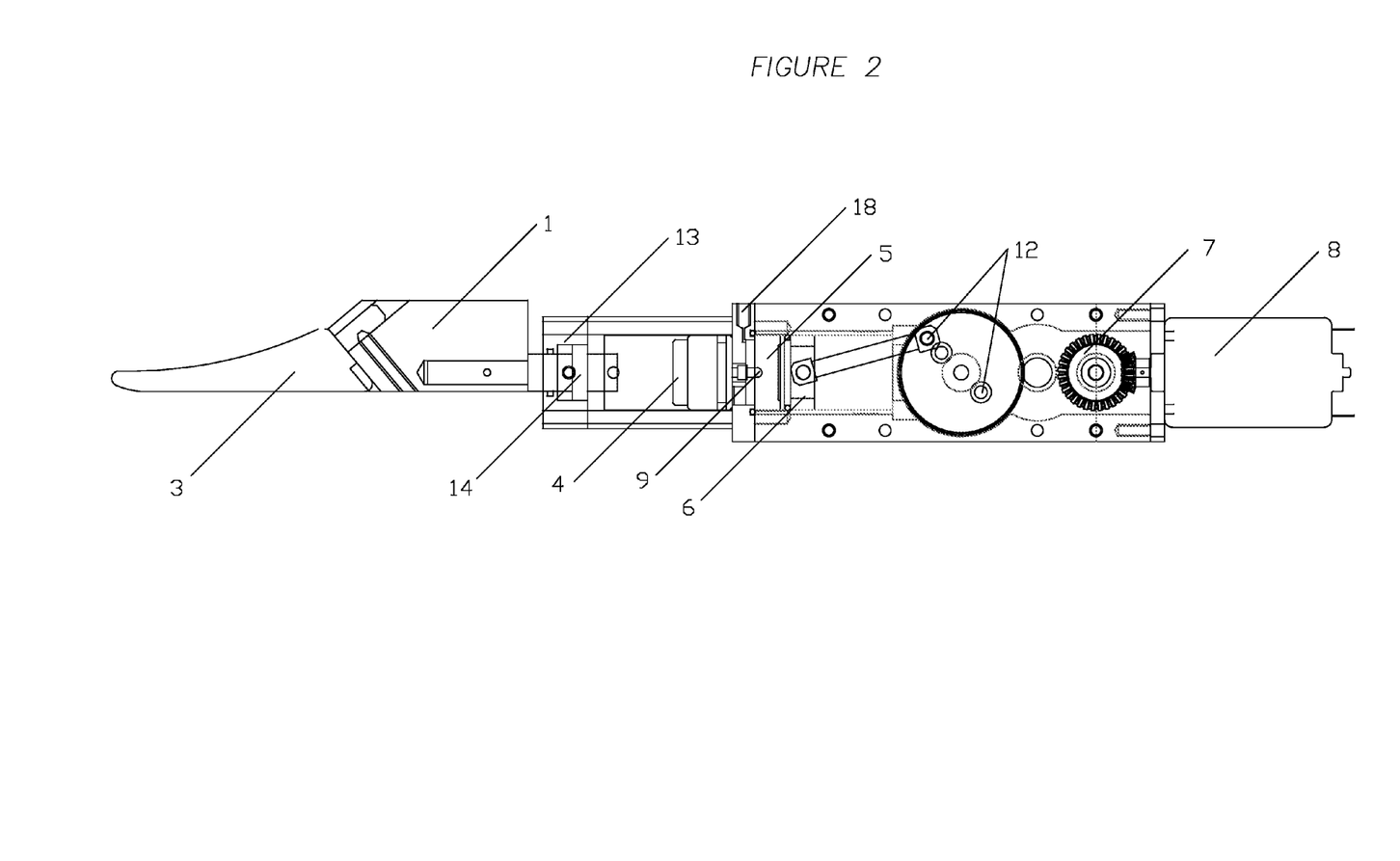
FIG. 2 shows a perspective view of a compression piston compressing air in the air compression chamber of the battery operated orthopedic impacting tool, in accordance with an exemplary embodiment of the present disclosure.
Figure 3:
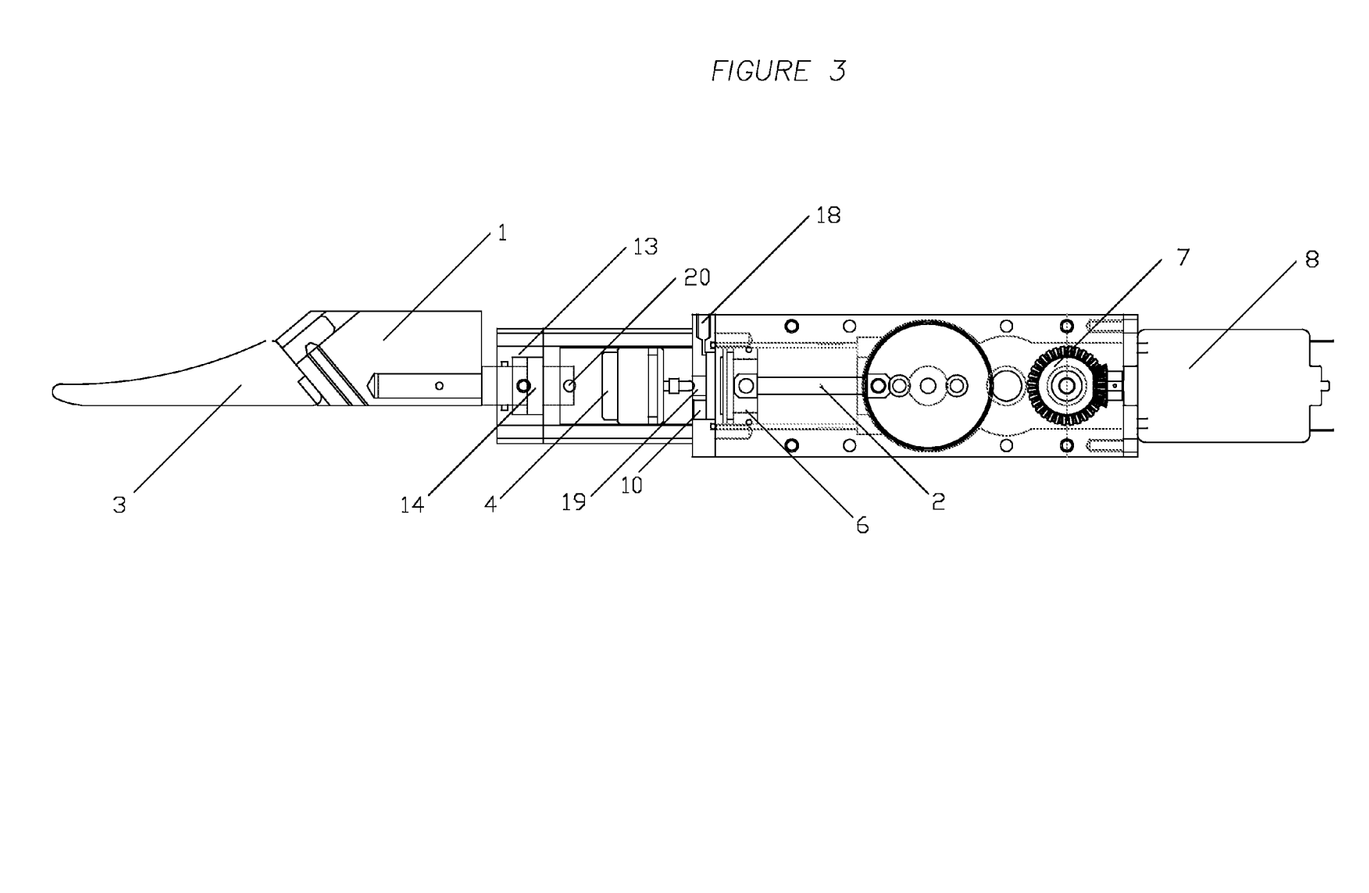
FIG. 3 shows the striker releasing from the magnetic detent and accelerating towards the anvil, in accordance with an exemplary embodiment of the present disclosure.
Figure 4:
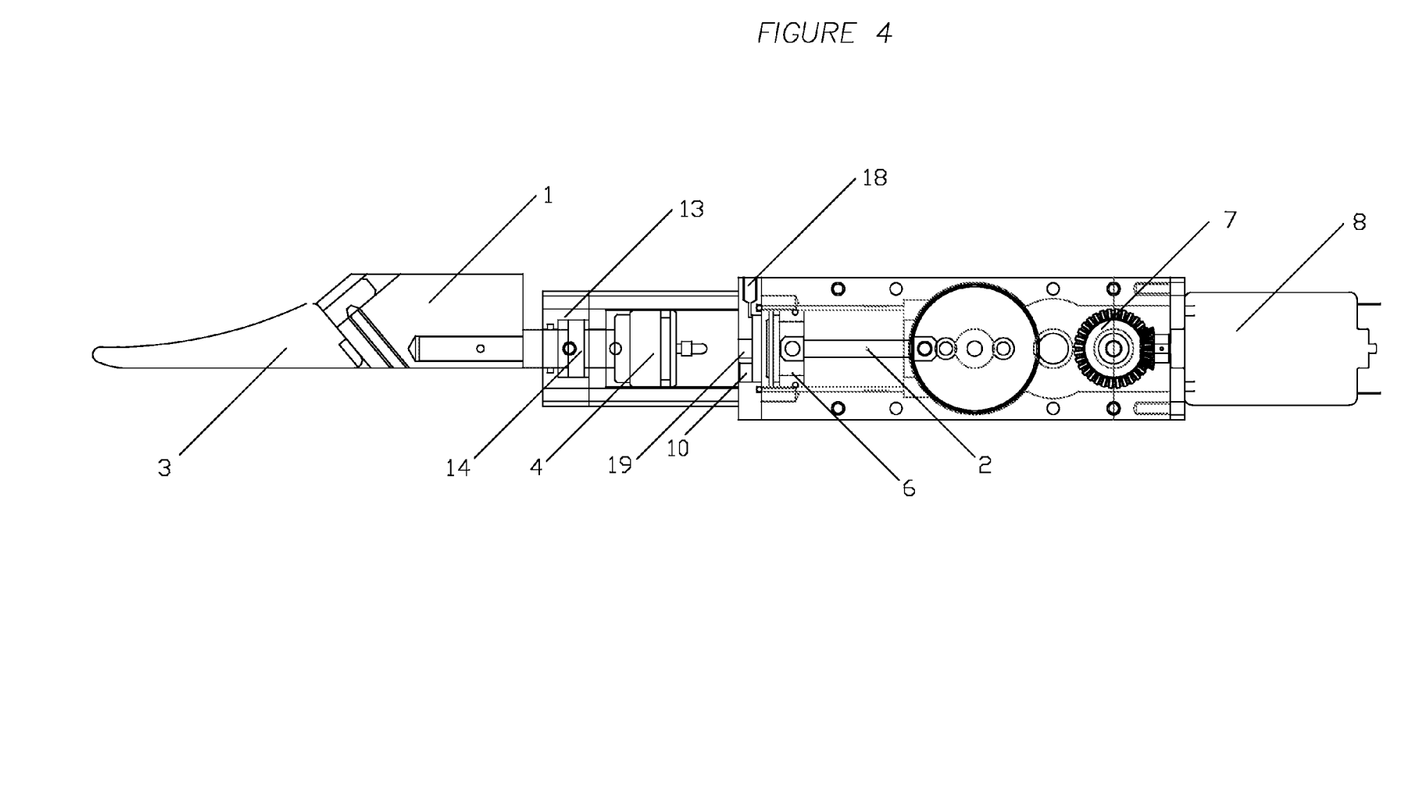
FIG. 4 shows the striker impacting the anvil causing the broach to be driven into a cavity, in accordance with an exemplary embodiment of the present disclosure.

In an embodiment, and referring now to FIG. 1, the linear motion converter 12 is comprised of a slider crank mechanism which slider crank is operatively coupled to the motor 8 and gear reducer 7. The tool further comprises an air compression chamber 5 that accepts a compression piston 6 which compression piston 6 is actuated by the linear motion converter 12. The air mass disposed between the forward portion of compression piston 6 and the striker nose 9 will be referred to as the "compression air chamber portion" or "compression air chamber" or "air compression chamber" 5.

In an embodiment of the present disclosure, the motor of the tool causes the linear motion converter to move the compression piston until sufficient pressure is built within the compression air chamber 5 that is disposed between the forward end of the compression piston and the striker nose 9 to overcome a detent 10 that otherwise retains the striker 4 in a rearward position. The detent 10 is any means of retaining the striker 4 in its rearward position while the air pressure builds in the compression air chamber 5. A further characteristic of the detent is that once it has been overcome, the retention force of the detent on the striker 4 reduces by at least 50% within the first 20% movement of the striker 4. This feature of force reduction unexpectedly allows the striker 4 to impact the anvil forward impact surface 16 or adapter with more then 50% increase in power.

In a further embodiment the motor of the tool causes the linear motion converter to move the compression piston until the compression piston moves sufficient distance that the forward portion of the piston 6 impacts the striker nose 9, overcoming the detent 10 that retains the striker 4 in the rear position. Once the striker 4 has been released from the detent, the compressed air in the compression air chamber 5 rushes through the air passageway 19 and the force of the air pressure accelerates the striker 4, which striker 4 slides axially down a cavity (which cavity comprises, in an embodiment, striker guide 11) internal to the tool housing and strikes the anvil forward impact surface 16 or adapter. The resultant force is communicated through the anvil 14 that is proximate to the impact surface 16 and, optionally, through the adapter 1 (which adapter will be described in more detail below) to which a broach, chisel, or other device for seating or removing an implant, or prosthesis may be attached. The striker guide 11 has air chamber vent holes 20 which allow the air in front of the striker to escape thus increasing the impact force of the striker 4 on the anvil 14.

Figure 5:
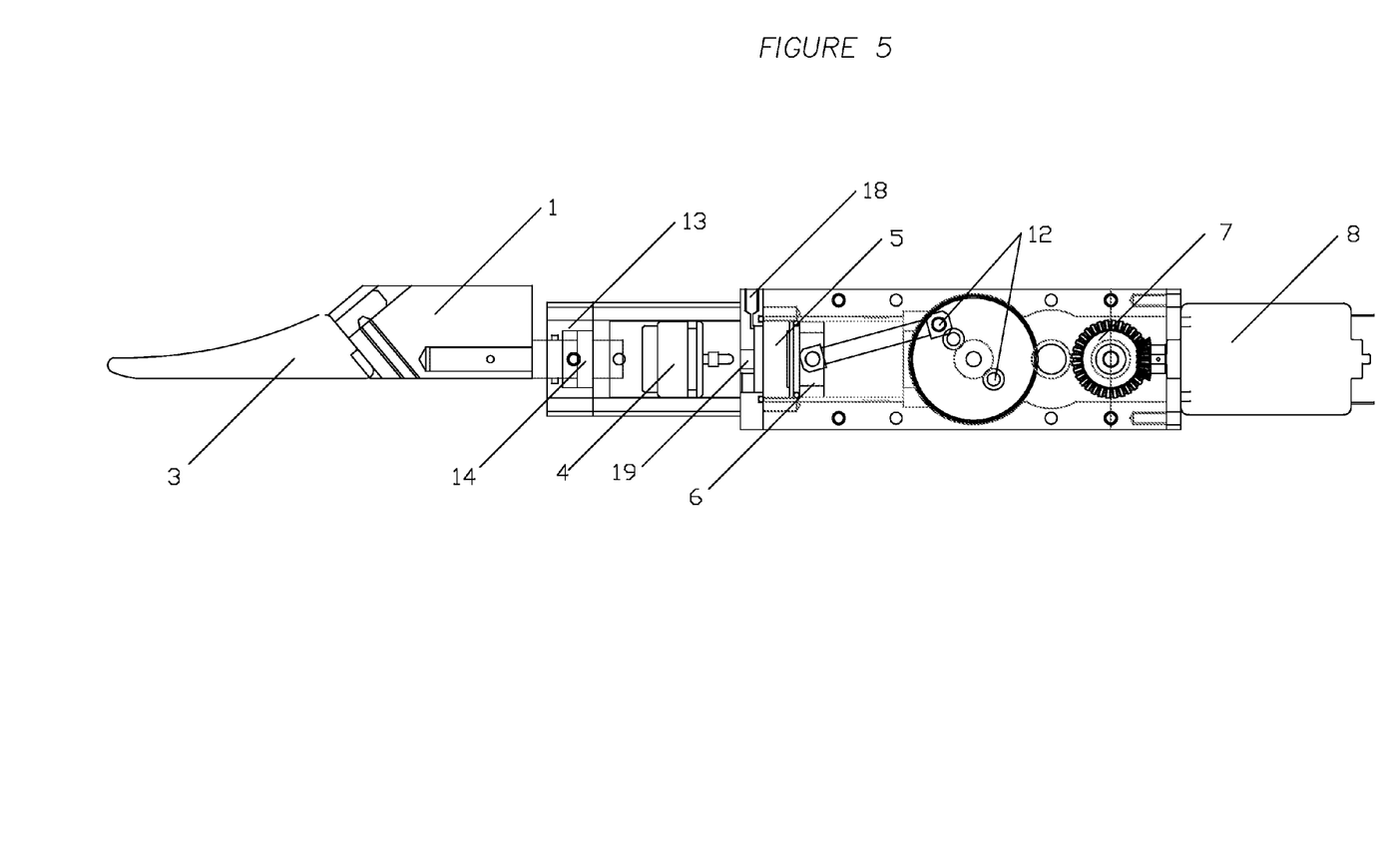
FIG. 5 shows the compression piston returning, thus creating a vacuum on the striker and causing the striker to shift direction and move rearward, in accordance with an exemplary embodiment of the present disclosure.
Figure 6:
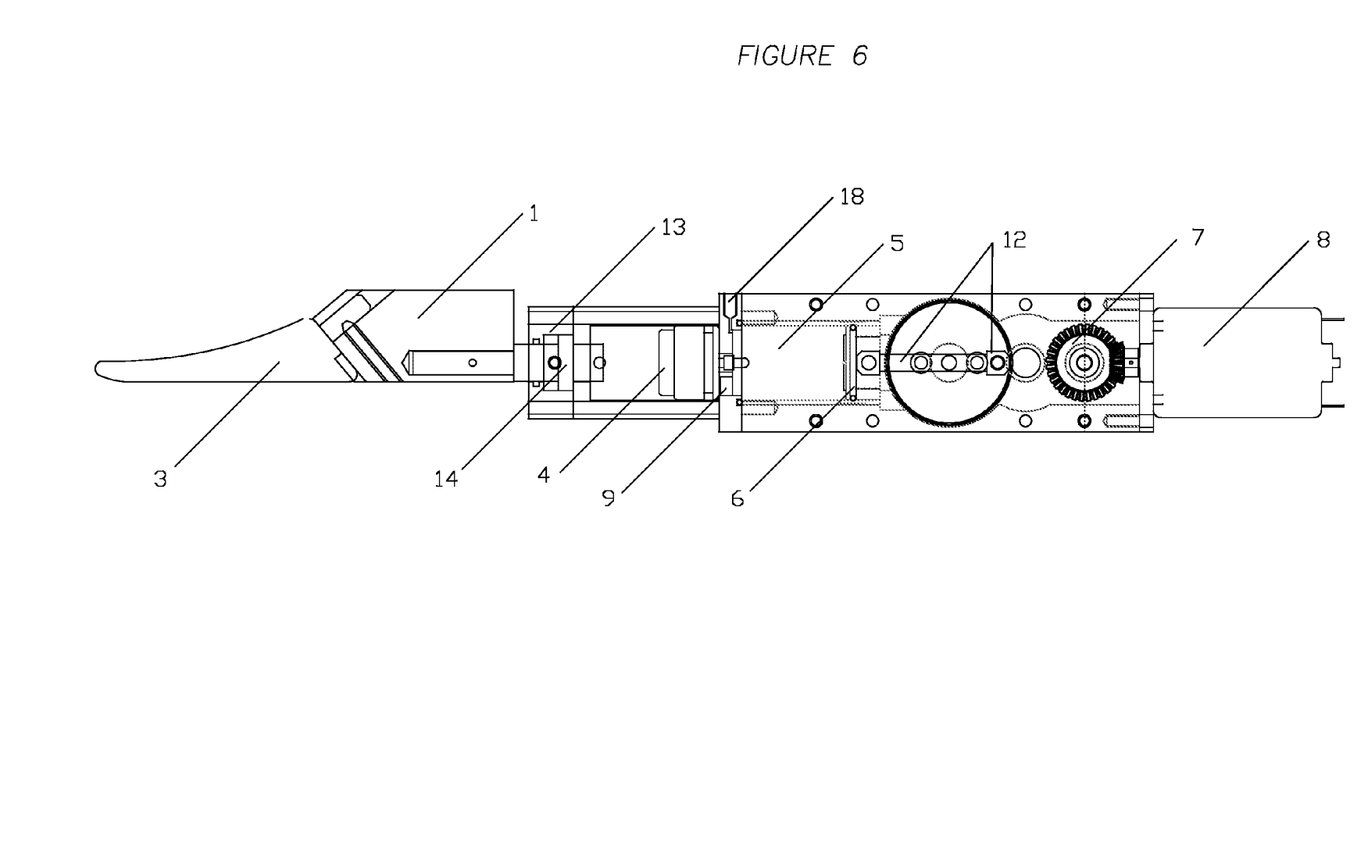
FIG. 6 shows the striker impacting the rear of the striker chamber in accordance with an exemplary embodiment of the present disclosure.

As the compression piston 6 continues through its stroke it moves towards the rear direction, which draws a vacuum on the compression air chamber 5 (as shown in FIGS. 5 and 6). Said vacuum is communicated through the air passageway 19, which communicated vacuum acts on the back side of striker 4. This causes the striker to reverse direction and accelerate towards the rear 15 of the striker guide 11 and eventually impact the rear 15 of striker guide 11. This communicates a rearward force to the tool and can be used to dislodge a broach which is stuck in a cavity for example. This vacuum may be assisted with a return spring (not shown) which biases the striker 4 towards the rear 15 of striker guide 11. Further, this allows the detent 10 to lock the striker 4 in position for another impact. The compression piston completes its rearward stroke and rests at or near bottom dead center of the compression air chamber. The compression air chamber may comprise openings in the sidewall thereof which allow replenishment of any air which has been lost. Thus in one complete cycle, a forward and/or rear directed impacting force can be applied on the broach, chisel, or other device, or implant/prosthesis. Additionally, it should be noted that the direction of the impact can be controlled by the user's force on the tool and the stroke limiter 13. For example, if the tool is being pulled away from the cavity, the striker will not impact the anvil (or broach adapter) but will impact the front of the striker guide, thus not communicating any forward thrust to the broach. Further, if this is maintained, the striker as it returns will impact the rear 15 of the striker guide 11 and thus communicate a removing force to the broach. Thus, another advantage of the tool is that the user may control the direction of the impacting by applying a bias on the tool. With the user being able to control the direction of the impact, her or she is able to control whether the adapter oscillates substantially back and forth or primarily in one direction. This has application for methods that require oscillation or impaction.

The slider crank embodiment of the tool facilitates controlled continuous impacting of the striker and anvil (or adapter). For such continuous impacting, after causing compression by the compression piston, the slider crank returns to the bottom of its stroke, which return pulls a vacuum on the striker and causes the striker to return to its initial rest position. For controlled continuous impacting, it will be apparent that this cycle may repeat indefinitely.

For a single stroke, the linear motion converter (such as the slider crank described herein) will stop at or near the rear position, thus releasing the forward pressure on the striker and allowing the striker to return it to its starting position in readiness for another stroke. In this operational mode, a user may cause the tool to impact selectively (as opposed to repeatedly), thus allowing further control of the impacts and the creation or shaping of the surgical area, for example.

In a further embodiment, a valve or other air bleed off means is used as a force adjuster 18. By allowing a certain amount of compressed air to bleed off during the forward movement of the piston 6, the amount of air available to accelerate the striker 4 is reduced, thus allowing for a reduced impact force on the anvil and broach. This force reduction is useful for older or weakened bones of a patient in that it the surgeon to effectively broach the bone without the risk of a hoop fracture, for example.

A sensor coupled operatively to the control means may be provided to assist in regulating a preferred cyclic operation of the linear motion converter. For example, the sensor may communicate at least one position to the control means allowing the linear motion converter to come to rest at or near the fully back position. This permits the tool to be in readiness to generate pressure for the next impact.

The control means is further capable of tuning the amount of impact force per cycle. By controlling the impact force the tool can avoid damage caused by uncontrolled impacts or impacts of excessive force. For example, a user may reduce the impact setting in the case of an elderly patent with osteoporosis, or may increase the impact setting for more resilient or intact athletic bone structures.

One such force control preferably comprises a selectable release setting on a detent that holds the striker. It will be apparent that the striker will impact the anvil or adapter with greater force in the case where the pressure needed to dislodge the striker from the detent is increased. In another embodiment, the detent may comprise a solenoid, which solenoid may activate upon a predetermined buildup of pressure, after which the striker 4 is released, allowing it to impact the anvil.

In a further embodiment, the compression air chamber may further include an adjustable or fixed leak that allows some of the compressed air to leak out of the chamber. This reduces the amount of air which is available to accelerate the striker thus reducing the impact force on the anvil. In the case of the adjustable leak, it will be apparent that adjusting the leak to maximum would give the lowest impact force from the striker and adjusting to shut the leak off (zero leak) would give the highest impact force from the striker.

The tool may further comprise a lighting element, and, in an embodiment, the lighting element may comprise an LED arrangement, which lighting element may be capable of illuminating a user's work area. In an embodiment, the LED may be disposed on the housing of the tool and may be oriented toward a patient's body or surgical cavity.

The tool may further comprise a plate or other flat surface at the end of the tool that is distal to the surgical area, which plate may allow a user to apply selective manual pressure on a broach, chisel or other device, or a surgical implant as dictated by surgical or physical conditions. For instance, if a broach is firmly lodged within a cavity such that the operation of the tool would not remove the broach, the user may manually tap on the plate to dislodge the broach.

The tool may further comprise a torsion sensor, which sensor may be capable of determining a lateral or deviating force or movement of the tool, such that if the tool is sensed to deviate from a pre-determined magnitude at the broach/implant interface, a signal may emit to notify the user of such deviation. In this manner and otherwise, the tool facilitates consistent axial broaching and implant seating.

In a further embodiment, the adapter may comprise a linkage arrangement. In this embodiment, the adapter may receive a broach for anterior or posterior joint replacement. The linkage mechanism of the adapter may facilitate receiving and orienting the broach in a variety of positions, such as in a centered position, or in an offset left or right position. The adapter will maintain the broach in an orientation that is parallel or co-linear to the body of the tool and the striker. The adapter may also comprise clamps, a vice, or any other fastener that may securely hold the broach, chisel, or other device, during operation of the tool.

The tool may further comprise a removable battery pack. This battery pack can be disposable or rechargeable. The advantage of a disposable battery pack is that it would not be subject to degradation caused by the sterilization cycles and that it could remain in sterile packaging until used.

The tool may further comprise handgrips disposed on the housing of the tool, which handgrips may include a rubberized or other tacky coating removably disposed thereon. Such coating facilitates comfortable operation of the tool and improves the user's hold on the tool for increased control thereof and reduced fatigue during operation of the tool.

In use, a user such as a surgeon firmly holds the tool by the handle grip or grips and utilizes light emitted by the LED to illuminate a work area and accurately position a broach, chisel or other device that has been attached to the tool on a desired location on the prosthesis or implant. The reciprocating movement imparted by the tool upon the broach, chisel or other device causes tapping of the implant and thereby enables proper seating or removal of the prosthesis or the implant into or out of an implant cavity. The warning system may alert the user in the event that a bending moment above a certain magnitude is detected at a broach (or chisel or other device)/implant interface.

The tool disclosed herein provides various advantages over the prior art. It facilitates controlled impacting at a surgical site, which minimizes unnecessary damage to a patient's body and which allows precise shaping of a implant or prosthesis seat. The tool also allows the user to modulate the direction and force of impacts, which improves the user's ability to manipulate the tool. The force control adjustment of the impact settings allows a user to set the force of impact according to a particular bone type or other profile of a patient. The tool thereby enables proper seating or removal of the prosthesis or the implant into or out of an implant cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. An orthopedic impacting tool for striking an object, the tool comprising
    a motor,
    a linear motion converter,
    a compression piston operatively coupled to said linear motion converter, said piston having a first end and a second end,
    an air compression chamber,
    a striker,
    a detent for retaining the striker in a position,
    a control means,
    an anvil element,
    an adapter capable of holding a broach, chisel, reamer, or other surgical implement, said adapter operatively coupled to said anvil element, and
    a hand grip,
    wherein said control means directs said motor to move said linear motion converter and causes said compression piston to move and compress or decompress air within said air chamber, and
    wherein when said compressed air exceeds the retention force of the detent the striker moves from a first position to a second position, striking said anvil element,
    such that the striker imparts a force upon the adapter in at least one direction.

2. The tool of claim 1, wherein said linear motion converter comprises one of a slider crank mechanism, rack and pinion mechanism, cam mechanism and a power screw.

3. The tool of claim 1, wherein the detent is selected from at least one of a mechanical detent, an interference fit, a magnet and a solenoid.

4. The tool of claim 1 wherein the control means allows for at least one of a single percussive impacting and a variable speed percussive impacting.

5. The tool of claim 1, wherein said tool further comprises a lighting element disposed on an exterior surface of the tool, said lighting element operatively coupled to the control means.

6. The tool of claim 1, wherein the control means receives input from at least one sensor.

7. The tool of claim 1, wherein the direction of the tool impact force depends upon the force placed on the tool by a user.

8. The tool of claim 1, wherein said tool further comprises a torsional sensor, which torsional sensor is capable of determining a lateral movement of the tool and which sensor is capable of signaling such movement or force.

9. The tool of claim 1, wherein said adapter comprises an offset adjustment for attachment of an attached broach, chisel, reamer, or other surgical implement away from the central axis of the tool.

10. An orthopedic impacting tool for striking an object, the tool comprising
    a motor,
    a linear motion converter,
    a compression piston operatively coupled to said linear motion converter, said piston having a first end and a second end,
    an air chamber, a striker, a nosepiece coupled to said striker, a detent for retaining the striker in a position, a control means, an anvil element, an adapter capable of holding a broach, chisel, reamer, or other surgical implement, said adapter operatively coupled to said anvil element, and a hand grip, wherein said control means directs said motor to move said linear motion converter and causes said compression piston to move and compress or decompress air within said air chamber, and wherein when said position of compression piston contacts said nosepiece of said striker with force that exceeds the retention force of the detent said striker moves from a first position to a second position, striking said anvil element, such that the striker imparts a force upon the adapter in at least one direction.

11. The tool of claim 10, wherein said linear motion converter comprises one of a slider crank mechanism, rack and pinion mechanism, cam mechanism and or a power screw.

12. The tool of claim 10, wherein the detent is selected from at least one of a mechanical detent, and interference fit, a magnet and or a solenoid.

13. The tool of claim 10, wherein the impact force of the striker can be adjusted with a force adjustment control.

14. The tool of claim 13, wherein force of impact can be reduced by allowing some of the air to leak from the air compression chamber.

15. The tool of claim 10, wherein said tool comprises a torsional sensor, which torsional sensor is capable of determining a lateral movement of the tool and which sensor is capable of signaling such movement or force.

16. The tool of claim 10, wherein the control means receives input from a sensor.

17. An orthopedic impacting tool for striking an object, the tool comprising a motor, a linear motion converter, a compression piston operatively coupled to said linear motion converter, said piston having a first end and a second end, an air chamber, a striker, a nosepiece coupled to said striker, a detent for retaining the striker in a position, a control means, an adapter capable of holding a broach, chisel, reamer, or other surgical implement, and a hand grip, wherein said control means directs said motor to move said linear motion converter and causing said compression piston to move and compress or decompress air within said air chamber, and wherein when said position of compression piston contacts said nosepiece of said striker with force that exceeds the retention force of the detent said striker moves from a first position to a second position, such that the striker imparts a force upon the adapter in at least one direction.

18. The tool of claim 17, wherein the detent is selected from at least one of a mechanical detent, and interference fit, a magnet and or a solenoid.

19. The tool of claim 17, wherein the control means receives input from a sensor.

* * * * *